United States Patent
Kim et al.

(10) Patent No.: US 7,268,252 B2
(45) Date of Patent: Sep. 11, 2007

(54) BINAPHTHOL DERIVATIVES AND THEIR USE IN OPTICAL RESOLUTION OR OPTICAL TRANSFORMATION

(75) Inventors: Kwan Mook Kim, Seoul (KR); Won Woo Nam, Seoul (KR); Hyun Jung Park, Seoul (KR); Jik Chin, Toronto (CA)

(73) Assignee: Green of Life Co., Ltd., Seoul (KR)

( * ) Notice: Subject to any disclaimer, the term of this patent is extended or adjusted under 35 U.S.C. 154(b) by 0 days.

(21) Appl. No.: 11/341,707

(22) Filed: Jan. 30, 2006

(65) Prior Publication Data

US 2006/0173211 A1 Aug. 3, 2006

(30) Foreign Application Priority Data

Feb. 1, 2005 (KR) .................... 10-2005-0009145

(51) Int. Cl.
*C07C 205/00* (2006.01)
*C07C 41/00* (2006.01)
*C07C 31/34* (2006.01)
*C07C 327/00* (2006.01)
*C07C 233/00* (2006.01)

(52) U.S. Cl. ..................... 562/553; 568/425; 568/631; 568/635; 568/841; 564/74; 564/78; 564/184; 564/218; 564/223

(58) Field of Classification Search ................ 562/553, 562/425, 631, 635, 841; 564/74, 78, 184, 564/218, 223
See application file for complete search history.

(56) References Cited

OTHER PUBLICATIONS

Kim et al., Enantioselective recognition of 1,2-amino alcohols by reversible formation of imines with resonance-assisted hydrogen bonds, Organic Letters, Jul. 2005, vol.7, No. 16, pp. 3525-3527.*

Laura Favretto et al, "Highly Regioselective Microwave-Assisted Synthesis of Enantiopure $C_3$-Symmetric Trialkanolamines," Tetrahedron Letters 43 (2002), pp. 2581-2584.

Jik Chin et al, "Chiral Shift Reagent for Amino Acids Based on Resonance-Assisted Hydrogen Bonding," Organic Letters (2004) vol. 6, No. 15, pp. 2591-2593.

Robert M. Williams et al., "Asymmetric Synthesis of Arylglycines," Chemical Reviews, (1992), vol. 92, pp. 889-917.

Keiji Maruoka et al, "Enantioselective Amino Acid Synthesis by Chiral Phase-Transfer Catalysis," Chemical Reviews, (2003), vol. 103, pp. 3013-3028.

Rudolf O. Duthaler, "Recent Developments in the Stereoselective Synthesis of α-Aminoacids", (1994), vol. 50, No. 6, pp. 1539-1650.

* cited by examiner

*Primary Examiner*—J. Parsa
(74) *Attorney, Agent, or Firm*—Dickstein Shapiro LLP

(57) ABSTRACT

Disclosed herein are novel binaphthol derivatives and methods for the optical resolution of amino acids or amino alcohols and for the optical transformation of D, L-forms of amino acids using the same.

7 Claims, 2 Drawing Sheets

[FIG. 3]
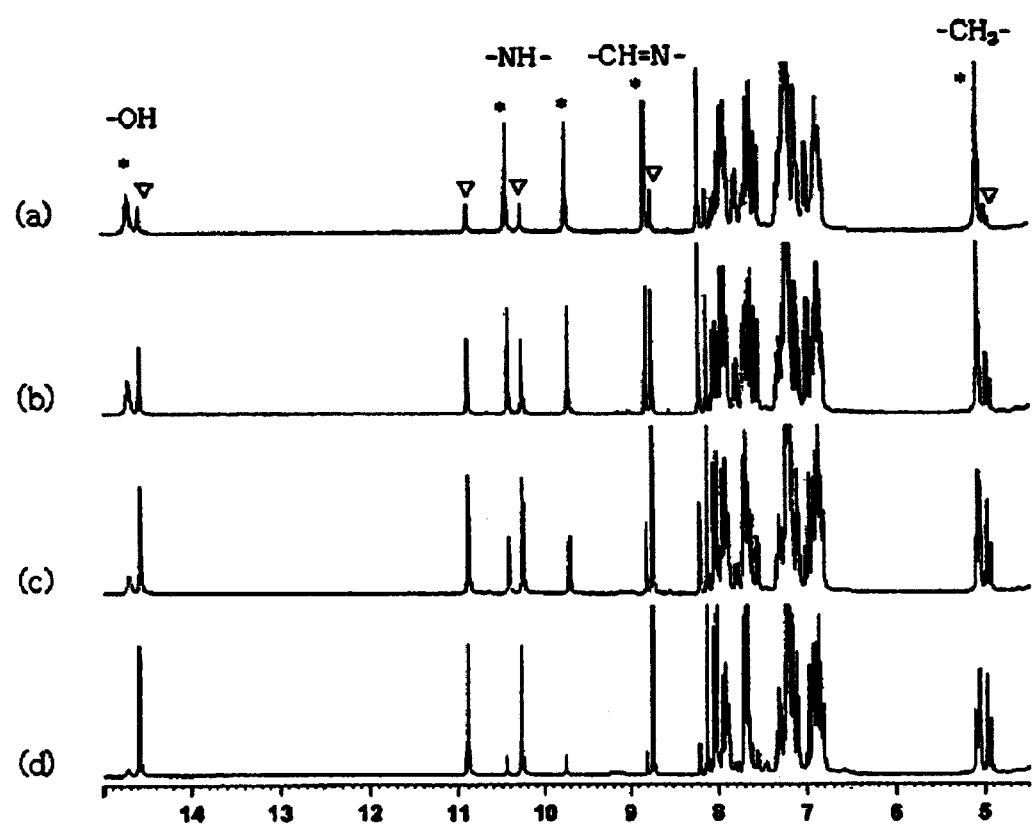

BINAPHTHOL DERIVATIVES AND THEIR USE IN OPTICAL RESOLUTION OR OPTICAL TRANSFORMATION

BACKGROUND OF THE INVENTION

1. Field of the Invention

The present invention relates to binaphtol derivatives, represented by the following chemical formula I, suitable for use in the optical resolution of racemic amino acids or racemic amino alcohols or in the optical transformation of amino acids from D-form into L-form or vice versa. Also, the present invention relates to uses of the derivatives in the optical resolution of racemic amino acids or racemic amino alcohols to afford optically pure amino acids or amino alcohols and in the optical transformation of amino acids from D-form into L-form or vice versa.

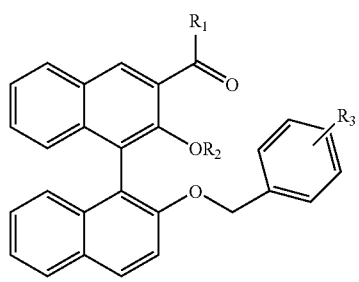

Chemical Formula I

2. Description of the Related Art

Found in useful applications such as ligands of asymmetric catalysts and building blocks necessary for the synthesis of various physiologically active materials, optically pure amino alcohols are industrially important compounds.

The preparation of optically pure amino alcohol is found in DE Pat. Publication No. 4341605 that discloses a method of synthesizing optically pure amino alcohol from optically pure amino acids. However, because D-form amino acids do not naturally occur, the requirement of the industrial synthesis therefor causes an increase in production cost. Accordingly, the amino alcohols corresponding thereto are also synthesized at an increased cost. Additionally, the method is disadvantageously applied only for the preparation of limited amino alcohols.

Favretto et al., (Tetraheron Lett. 2002, 43, 2581) suggested a method of synthesizing optically pure amino alcohol from chiral epoxide. This method, however, suffers from the disadvantages of having to use expensive chiral epoxide and being poor in yield, regioselectivity, and sterespecificity; thus, this method has a limitation in industrial application.

For that reason, the separation of optically pure amino alcohol from a synthesized racemate may be useful.

In the present invention, an imine bond is first utilized to recognize the chirality of chiral amino alcohols, thereby separating optically pure amino alcohols.

An imine bond, which is a covalent bond that is formed by a reaction of aldehyde with amine, is stronger than non-covalent bonds, but weaker than general covalent bonds, so that it can be reversibly formed. Thus, when chiral amine is recognized through the formation of imine, the strong covalent bond is advantageous to the separation of racemic amino alcohol to each chiral amino alcohols while the reversible formation of the imine bond is very useful in isolating the chiral amino alcohols recognized and separated through the imine bond. However, little study has been done about the separation of chiral amino alcohol through an imine bond.

Meanwhile, study on the use of the compound of the following chemical formula II in recognizing the chirality of amino acids or amino alcohols is disclosed in Org. Lett. Vol. 6, p 2591. The compound readily reacts with amino acids to form imines that exhibit different NMR spectra according to whether the reacted amino acids are in D-form or L-form.

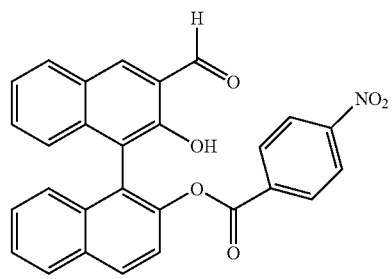

[Chemical Formula II]

Although the compound of the chemical formula II is useful in differentiating the D-form and L-form of amino acids by NMR, two imines resulting from the reaction of D-form or L-form amino acids therewith are not largely different in stability so that the ratio thereof is no more than 1.2:1. Hence, the compound of the chemical formula II is possible to use as an NMR chiral shift reagent, but impossible to use in separating racemic amino acids or racemic amino alcohols into D- and L-forms. Additionally, the ester linkage between the naphthalene group and the phenyl group in the compound is apt to be readily hydrolyzed.

Amino acids are the basic structural unit of peptides and proteins, which are the major structural components of all body tissues, and the optically pure forms thereof can be used in various purposes. However, because amino acids that naturally occur are only in L-form, D-form amino acids do not meet the demand. Extensive research has been done for methods of preparing pure D-form amino acids at ease and at low cost. Many methods have been developed for preparing optically pure amino acids ((a) Williams, R. M.; Hendrix, J. A. *Chem. Rev.* 1992, 92, 889. (b) Duthaler, R. O. *Tetrahedron* 1994, 50, 1539. (c) Maruoka, K.; Ooi, T. *Chem. Rev.* 2003, 103, 3013.), but nowhere has the optical transformation of amino acids from L-form to D-form been reported, thus far.

SUMMARY OF THE INVENTION

Leading to the present invention, intensive and thorough research into optical resolution and optical transformation, conducted by the present inventors, resulted in the finding that non-ester linkage between rings of a chriality recognizable compound is resistant to hydrolysis and the chriality recognizable compound can perform optical resolution and optical transformation stably.

It is an object of the present invention to provide a novel compound, which is stable to hydrolysis and able to effectively perform the optical resolution of amino acids or amino alcohols into their D- and L-forms.

It is another object of the present invention to provide a method for interconverting D-form amino acid and L-form amino acid.

BRIEF DESCRIPTION OF THE DRAWINGS

The above and other objects, features and advantages of the present invention will be more clearly understood from the following detailed description taken in conjunction with the accompanying drawings, in which:

FIG. 3 shows $^1$H NMR spectra of an imine compound resulting from the reaction of an S-binaphthol derivative of Compound 5 with L-alanine in the presence of 3 equivalents of $Et_3N$, taken immediately after the reaction (a), 2 hours after the reaction (b), 3 hours after the reaction (c) and 48 hours after the reaction (d), wherein mark * denotes peaks of imine compound produced from L-alanine and mark ∇ denotes peaks of imine compound produced from D-alanine.

DESCRIPTION OF THE PREFERRED EMBODIMENTS

Figure 1:
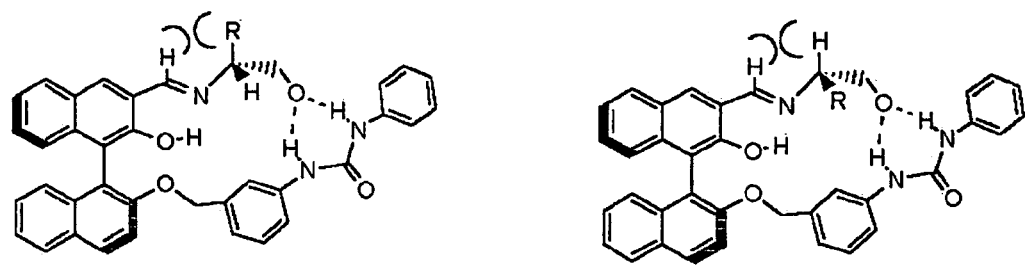
FIG. 1 shows structures of an imine compound, which are minimal in energy as measured by molecular mechanics computation.

The present invention pertains to the compound represented by the following chemical formula I.

[Chemical Formula I]

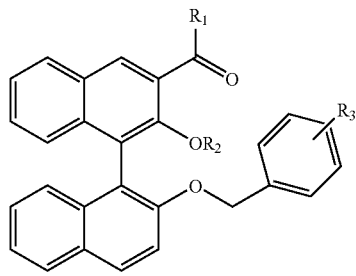

wherein R1 and R2 each is Hydrogen, a straight or branched alkyl substitutable with halogen or OH, a cyclic alkyl substitutable with halogen or OH, alkenyl, alkynyl, or an aryl substitutable with halogen or OH; and R3 is NHCXR4 or $NHCHNH_2^+$, wherein X is an oxygen or sulfur atom, and R4 is a straight or branched alkyl substitutable with halogen, NR5R6, or OR7, wherein R5 to R7 each is hydrogen, a straight or branched alkyl substitutable with halogen, or an aryl. If R3 is $NHCHNH_2^+$, the counter ion is halogen ion, preferably $Cl^-$ or $R13COO^-$ wherein R13 is alkyl or aryl, preferably $CH_3$.

The compound exists as one of the following isomers.

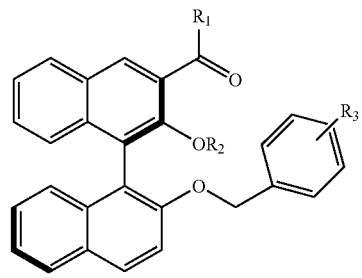

R-binaphthol derivative

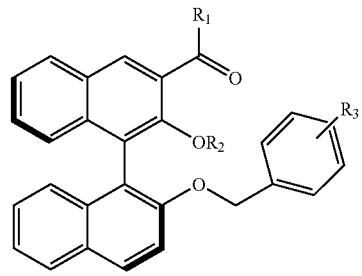

S-binaphthol derivative

Also, the present invention pertains to a method for the optical resolution of racemic amino alcohols or racemic amino acids using the compound of Chemical Formula I.

Also, the present invention pertains to a method for the optical transformation of amino acids from D-form to L-form and vice versa using the compound of Chemical Formula I.

In the compound of Chemical Formula I, the alkyl preferably contains 1 to 10 carbon atoms and more preferably 1 to 5 carbon atoms.

Preferred compounds of the present invention are given in Table 1, below.

TABLE 1

| Compounds | R1 | R2 | R3 |
|---|---|---|---|
| Compound 1 | H | H | $NHCOCH_3$ |
| Compound 2 | H | H | $NHCOC_2H_5$ |
| Compound 3 | H | H | $NHCONH_2$ |
| Compound 4 | H | H | $NHCONHCH_3$ |
| Compound 5 | H | H | $NHCONHC_6H_5$ |
| Compound 6 | H | $CH_3$ | $NHCOCH_3$ |
| Compound 7 | H | $CH_3$ | $NHCOC_2H_5$ |
| Compound 8 | H | $CH_3$ | $NHCONH_2$ |
| Compound 9 | H | $CH_3$ | $NHCONHCH_3$ |
| Compound 10 | H | $CH_3$ | $NHCONHC_6H_5$ |
| Compound 11 | $CH_3$ | H | $NHCOCH_3$ |
| Compound 12 | $CH_3$ | H | $NHCONHCH_3$ |
| Compound 13 | $CH_3$ | H | $NHCONHC_6H_5$ |
| Compound 14 | $CH_3$ | $CH_3$ | $NHCOCH_3$ |
| Compound 15 | $CH_3$ | $CH_3$ | $NHCONHCH_3$ |
| Compound 16 | $CH_3$ | $CH_3$ | $NHCONHC_6H_5$ |
| Compound 17 | H | H | $NHCSNHCH_3$ |
| Compound 18 | H | H | $NHCSNHC_6H_5$ |
| Compound 19 | H | H | $NHCHNH_2^+$ |
| Compound 20 | $C_6H_5$ | H | $NHCONHC_6H_5$ |

A description is given of the preparation of the compound, below.

Although any method may be used, the compound of Chemical Formula I is preferably prepared according to the following Scheme 1 in which synthesizable (S)-2,2'-binaphthol-3-aldehyde is reacted with acylaminobenzylhalide or phenylurylbenzylhalide in the presence of a base. In addition, the compounds thus obtained can be used to produce other compounds of the present invention by changing the hydroxy group into an alkoxy group in a typical manner.

Instead of binaphthol aldehyde, various binaphthol ketones may be used as a starting material.

following chemical formula III and has an intramolecular asymmetric carbon center that gives rise to the enantiomeric R- and S-forms.

$NH_2CHR8CR9R10OH$                                   Chemical Formula III wherein, R8 is not hydrogen but a monovalent organic group or halogen, and is preferably a substituted or non-substituted

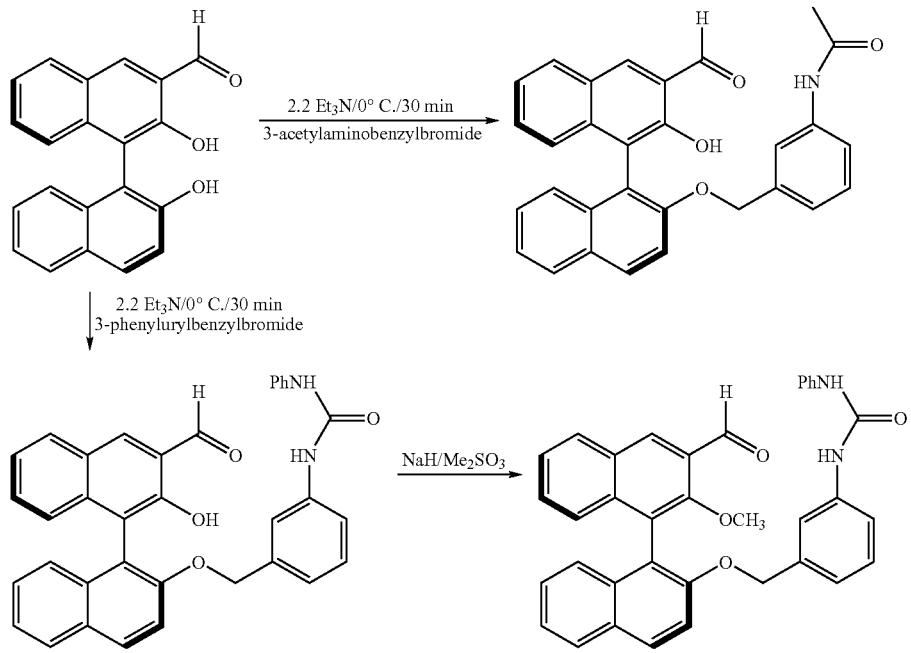

Scheme 1

Although illustrated with S-binaphthol derivative, Scheme 1 can be also applied to R-binaphthol derivative.

The reaction can be conducted in a typical solvent in the presence of a typical base.

Examples of the solvent for the reaction include N,N-dimethylformamide (DMF), tetrahydrofuran (THF), and $CH_2Cl_2$, with preference for DMF.

Organic or inorganic bases, such as $NEt_3$, NaH, NaOH, etc., may be used for the reaction, with $NEt_3$ or NaH being preferred.

The reaction is carried out at 0-30° C. and preferably at room temperature.

The compounds of the present invention are suitable for use in the optical resolution of racemic amino alcohols or racemic amino acids.

Having an aldehyde or ketone group, the compound according to the present invention can react with various amine groups to form imines. Also, the amide group of the compound according to the present invention forms a stronger hydrogen bond with the carboxylate group ($—CO_2^-$) of amino acid or the hydroxy group (—OH) of amino alcohol than does the —$NO_2$ group of the compound disclosed in the literature (Org. Lett., supra)

The amino alcohol that can be optically resolved by the compound of the present invention is represented by the alkyl, a substituted or non-substituted alkenyl, a substituted or non-substituted cyclic alkyl, or a substituted or non-substituted aryl, and R9 and R10 each are hydrogen, a substituted or non-substituted alkyl, a substituted or non-substituted alkenyl, a substituted or non-substituted cyclic alkyl, or a substituted or non-substituted aryl.

The compound of the present invention can be applied for the optical resolution of the amino acid represented by the following chemical formula IV.

$NH_2CHR11COOR12$                                   Chemical Formula IV wherein, R11 is not hydrogen but a monovalent organic group or halogen, and is preferably a substituted or non-substituted alkyl, a substituted or non-substituted alkenyl, a substituted or non-substituted cyclic alkyl, or a substituted or non-substituted aryl, and R12 is hydrogen, a substituted or non-substituted alkyl, a substituted or non-substituted alkenyl, a substituted or non-substituted cyclic alkyl, or a substituted or non-substituted aryl.

Any method known in the art can be used for the optical resolution of racemic amino alcohols or racemic amino acids using the compound of Chemical Formula I. For example, the optical resolution can be achieved in a batch type manner using a solvent or in a column where the compound is filled.

Additional optical resolution, if necessary, may be conducted with the primarily optically resolved amino alcohol or amino acid so as to afford optically purer amino alcohol or amino acid.

The compound of the present invention can be used to transform the amino acid of Chemical Formula IV from D-form to S-form and vice versa. With the aid of the S-binol derivatives of the present invention, L-form amino acid can be converted into D-form amino acid while the R-binol derivatives of the present invention can be applied for the transformation of D-form amino acid into L-form amino acid, which is based on the chirality recognition of the chiral compound.

A better understanding of the present invention may be obtained through the following examples which are set forth to illustrate, but are not to be construed as the limit of the present invention.

EXAMPLES

Example 1

Preparation of S-Binaphthol Derivative of Compound 1

(S)-2,2'-Binaphthol-3-aldehyde was reacted with 3-acetylaminobenzyl bromide in DMF for one hour in the presence of NaH. After extraction using water and chloroform, an organic layer was recovered and subjected to column chromatography to separate the title compound.

$^1$H NMR (CDCl$_3$) δ10.38(s, 1H), 10.20(s, 1H), 8.30(s, 1H), 6.8~8.0(m, 15H), 5.08(s, 2H), 2.13(s, 3H).

Example 2

Preparation of R-Binaphthol Derivative of Compound 1

The same procedure as in Example 1 was conducted with the exception that (R)-2,2'-binaphthol-3-aldehyde was used instead of (S)-2,2'-binaphthol-3-aldehyde.

Example 3

Preparation of S-Binaphthol Derivative of Compound 5

The same procedure as in Example 1 was conducted with the exception that 3-phenylurylbenzyl bromide was used instead of 3-acetylaminobenzyl bromide.

$^1$H NMR (C$_6$D$_6$) δ10.93 (s, 1H), 9.74 (s, 1H), 8.79 (s, 1H), 8.51(s, 1H), 6.6~8.0(m, 20H), 4.89(dd, 2H).

Example 4

Preparation of Compound 10

After the addition of NaH thereto, Compound 5 was reacted with methane sulfonate in DMF at room temperature for one hour. The reaction mixture was extracted using water and chloroform and, thereafter, an organic layer was recovered, followed by the separation of the title compound through column chromatography.

$^1$H NMR (CDCl$_3$) δ10.48(s, 1H), 8.52(s, 1H), 6.7~8.0(m, 21H), 5.07(dd, 2H), 3.45(s, 3H).

Example 5

Preparation of Compound 13

After being protected with —CH$_2$OCH$_3$ (MOM) at the two —OH groups of (S)-2,2'-binaphthol, the protected (S)-2,2'-binaphthol was mixed with 1.2 equivalents of n-butyl lithium at −15° C. in THF by stirring for one hour. The temperature was further decreased to −78° C. before the addition of 1.2 equivalents of acetaldehyde to the mixture, and then was slowly raised to room temperature. After reaction for 4 hours at room temperature, NH$_4$Cl/H$_2$O was added. Extraction using chloroform gave an alcohol compound, MOM protected-3-(1-hydroxyethyl)-(S)-2,2'-binaphthol, which was then oxidized with Fe/NH$_4$Cl. Extraction using water and chloroform was followed by the recovery of an organic layer which was then subjected to column chromatography to afford MOM protected-3-acetyl-(S)-2,2'-binaphthol. This compound was deprotected and reacted with NaH/phenylurylbenzyl bromide. The reaction mixture was extracted using water and chloroform and an organic layer was recovered, followed by the separation of the title compound through column chromatography.

$^1$H NMR (CDCl$_3$) δ9.9 (s, 1H), 8.48 (s, 1H), 6.7~8.0 (m, 21H), 5.09 (dd, 2H), 2.25 (s, 3H).

Example 6

Preparation of Compound 20

Compound 20 was prepared in a manner similar to that for Compound 13, except for using benzaldehyde instead of acetaldehyde.

$^1$H NMR (CDCl$_3$) δ10.2(s, 1H), 8.70(s, 1H), 6.7~8.0(m, 26H), 5.09(dd, 2H).

Example 7

Optical Resolution by Molecular Mechanics Computation

It was expected by molecular mechanics computation, with the aid of the software Spartan '02 for Windows, available from Wavefunction Inc., that the imine resulting from the reaction of the S-binaphthol derivative of Compound 5 with R-amino alcohol is different in stability from that resulting from the reaction of the S-binaphthol derivative of Compound 5 with S-amino alcohol (see FIG. 1).

This computation indicates that, with regard to the stability of the imine compound formed by the reaction of Compound 5 with chiral aminopropanol, the imine compound formed by the reaction of Compound 5 with R-aminopropanol is approximately 3 kcal/mol more stable than the imine compound formed by the reaction of Compound 5 with S-aminopropanol. This stability difference is believed to be attributed to the steric hindrance between the imine proton and the amino alcohol. As seen in FIG. 1, there is steric hindrance between the imine proton and the alpha proton of the amino alcohol in the R-form and between the imine proton and the alkyl group of the amino alcohol in the S-form. Accordingly, the imine compound formed from S-aminopropanol becomes more unstable than the imine compound formed from R-form. In fact, the formation of an imine bond occurs 4-5 times better between Compound 5 and the R-form than between Compound 5 and the S-form.

Despite the stability difference, the imine is maintained in the two structures thanks to the resonance assisted hydrogen bond (RAHB) between the imine group and the —OH group and the hydrogen bond between the —OH group of the amino alcohol and —NH group of the uryl group. These two hydrogen bonds, in our opinion, serve to fix the entire conformation of the imines in the structures shown in FIG. 1, leading to the difference in stability due to the above-mentioned steric hindrance.

Example 8

Optical Resolution of Amino Alcohol

The S-binaphthol derivative of Compound 5 was tested for the optical resolution of (R,S)-2-aminopropanol. (R,S)-2-aminopropanol with molar ratio of 1:1 R-form:S-form was reacted with Compound 5 in benzene-$d_6$ to produce an imine compound, which was then analyzed using $^1$H-NMR, as shown in (d) of FIG. 2. For comparison, $^1$H-NMR spectra are shown in (a) of FIG. 2 for Compound 5, in (b) of FIG. 2 for the imine compound resulting from the reaction of Compound 5 with (S)-2-aminopropanol, and in (c) of FIG. 2 for the imine compound resulting from the reaction of Compound 5 with (R)-2-aminopropanol.

Figure 2:
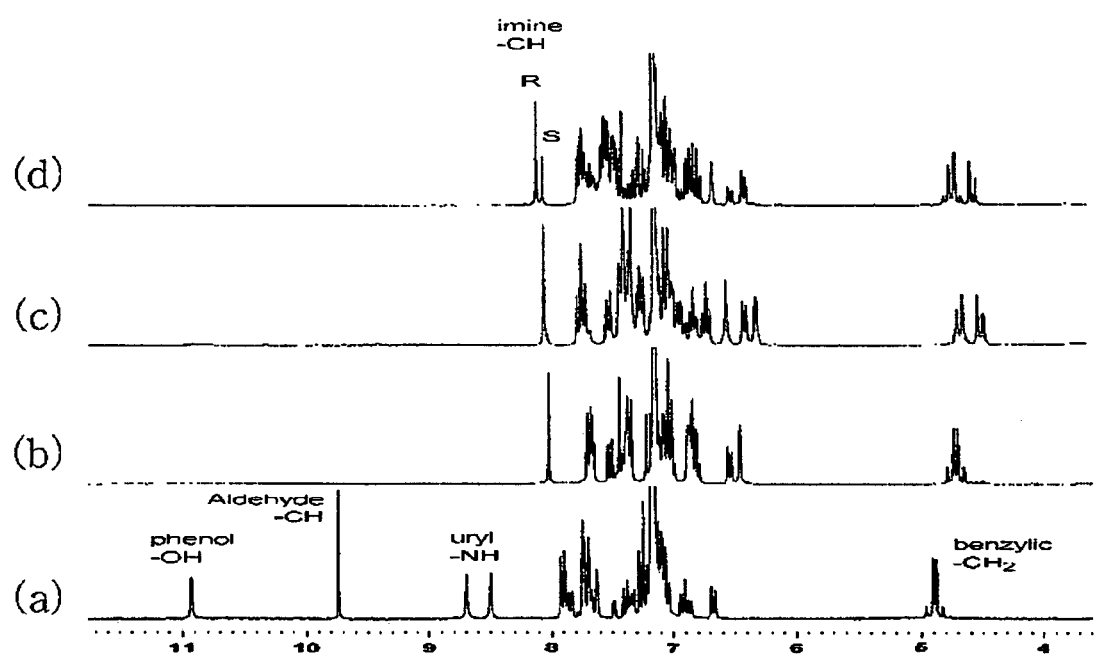
FIG. 2 shows $^1$H NMR spectra, measured in benzene-$d_6$, of Compound 5 in (a), an imine compound resulting from the reaction of Compound 5 with (S)-2-aminopropanol in (b), an imine compound resulting from the reaction of Compound 5 with (R)-2-aminopropanol in (c), and an imine compound resulting from the reaction of Compound 5 with 2 equivalents of (R,S)-2-aminopropanol in (d)

As it is apparent from the $^1$H NMR of (d) of FIG. 2 for the imine compound formed between Compound 5 and racemic aminopropanol, selectivity is found between the R-form and the S-form. When originating from R- and S-form amino alcohols, the proton peaks appear at 8.2 ppm and 8.1 ppm, respectively, as shown in (b) and (c) of FIG. 2. Thus, the R- and S-form that form imine bonds with Compound 5 can be quantitatively analyzed by measuring the intensities of peaks at 8.2 ppm and 8.1 ppm in the spectrum of (d) of FIG. 2. The $^1$H NMR spectrum of (d) demonstrates that the peak corresponding to the imine of R-form is 1.9 times higher than that corresponding to the imine of S-form. In this experiment, two equivalents of racemic amino alcohols to compound 5 were used, hence, R-form amino alcohol forms an imine bond with Compound 5 $1.9^2=3.8$ times better than does S-form amino alcohol. This result that R-form forms imine bond better than S-form agrees with the expectation that was proposed by the data obtained from the molecular mechanics computation of Example 5. The results are summarized in Table 2, below.

Example 9

Optical Resolution of Other Amino Alcohols

Other amino alcohols were tested for optical resolution in the same manner as in Example 8 and the results are given in Table 2, below. As indicated from the data of Table 2, Compound 5 shows no chiral selectivity for methylbenzylamine, which is believed to be attributed to the fact that methylbenzylamine has no groups able to form a hydrogen bond. This reflects that the selectivity mechanism postulated in the present invention is very appropriate for the elucidation of the optical resolution.

TABLE 2

| Compound | d, ppm R | d, ppm S | d, ppm R | d, ppm S | selectivity R:S |
|---|---|---|---|---|---|
| Methylbenzylamine | 7.96 | 7.96 | 4.71/4.65 | 4.80/4.72 | 1:1 |
| 2-amino-1-propanol | 8.21 | 8.13 | 4.85/4.66 | 4.88/4.79 | 3.8:1 |
| 2-amino-1-butanol | 8.25 | 8.08 | 4.81/4.61 | 4.77/4.69 | 3.1:1 |
| 2-amino-3-phenyl-1-propanol | 8.01 | 7.97 | 4.84/4.64 | 4.92/4.83 | 4.9:1 |

TABLE 2-continued

| Compound | d, ppm R | d, ppm S | d, ppm R | d, ppm S | selectivity R:S |
|---|---|---|---|---|---|
| 2-amino-2-phenylethanol | 8.25 | 8.16 | 4.84/4.61 | 4.84/4.77 | 4.6:1 |

In contrast, Compound 5 exhibits outstanding chiral selectivity for various amino alcohols that have therein —OH groups capable of forming a hydrogen bond, resulting from the superior ability thereof to recognize chirality of amino alcohols to that of conventional compounds. In addition, the existence of an ether group rather than an ester group in the compound increases the stability of the compounds of the present invention, giving rise to an improvement in their industrial applicability.

Example 10

Transformation of L-Alanine into D-Alanine

Using the compounds of the present invention, L-alanine was converted into D-alanine as analyzed by $^1$H NMR spectra of FIG. 3.

In FIG. 3, an imine compound resulting from the reaction of an S-binaphthol derivative of Compound 5 with L-alanine in the presence of 3 equivalents of $Et_3N$ was $^1$H NMR-analyzed immediately after the reaction (a), 2 hours after the reaction (b), 3 hours after the reaction (c) and 48 hours after the reaction (d). As seen in these spectra, new peaks appear just after the reaction, which coincide with those of the imine formed between Compound 5 and D-alanine. 48 hours after the reaction, the peaks detected in D-alanine predominated over those detected in L-alanine, indicating that L-alanine was transformed into D-alanine. As known from the spectra of FIG. 3, 90% of L-alanine was converted into D-alanine through a reaction between Compound 5 and L-alanine after 48 hours. In contrast, transformation from D-alanine to L-alanine seldom occurred. The reason for this is because Compound 5 is an S-binaphthol derivative. On the other hand, therefore, D-amino acid can be converted into L-amino acid using an R-binaphthol derivative. In consequence, the compounds of the present invention can be used to obtain optically pure D-amino acid or L-amino acid from recemic amino acid.

Example 11

Transformation of Other L-Amino Acids into D-Amino Acids

The same procedure as in Example 10 was conducted on other amino acids, and the ratios of L-amino acid to D-amino acid in the final products are given in Table 3, below. Taken together, the data shows that Compound 5 can be applied for the transformation of all natural and synthetic amino acids.

TABLE 3

| Amino acids | D-form/L-form |
|---|---|
| Threonine | 19.6/1 |
| Glutamine | 14.8/1 |

TABLE 3-continued

| Amino acids | D-form/L-form |
| --- | --- |
| Histidine | 13.9/1 |
| Arginine | 13.6/1 |
| Asparagine | 13.0/1 |
| Tyrosine | 12.3/1 |
| Phenylalanine | 11.1/1 |
| Methionine | 10.9/1 |
| Glutamic acid | 10.8/1 |
| Serine | 10.6/1 |
| Leucine | 9.4/1 |
| Tryptophan | 8.1/1 |
| Alanine | 6.9/1 |
| Aspartic acid | 2.0/1 |
| Isoleucine | 1.1/1 |
| Valine | 0/1 |

Example 12

Acquisition of D-Amino Acid from Imine Compound

The S-binaphthol derivative of Compound 5 was reacted with L-phenylalanine in $CDCl_3$ to form an imine, 48 hours after which D-phenylalanine appeared at the ratio shown in Table 3 from D-phenylalanine via the imine. The addition of $HCl/H_2O$ to the chloroform solution was found to concentrate phenylalanine in the aqueous layer and Compound 5 in the chloroform layer as analyzed by $^1H$ NMR. The ratio of D-form:L-form of the phenylalanine in the aqueous layer was the same as found in Table 3. When the amino acid in the chloroform was extracted twice with $HCl/H_2O$, the first extraction contained L-form in a higher quantity, but the second extraction was almost pure D-form, indicating that a pure D-form of amino acid can be obtained from a pure L-form although a little loss occurs during the transformation. In addition, Compound 5 in the remaining chloroform layer can be used to react with fresh amino acid in the same manner as above to afford D-amino acid and vice versa.

In addition to being far superior in recognizing chirality by use of an imine bond to other conventional compounds, the binaphthol derivatives of the present invention can be applied to all general chiral amino alcohols and amino acids. The compounds of the present invention, whether alone or in a chiral column, can be used to divide racemic compounds into optically pure forms. Also, the compounds of the present invention are capable of transforming L-amino acids into D-amino acids.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A binaphthol derivative, represented by the following chemical formula I:

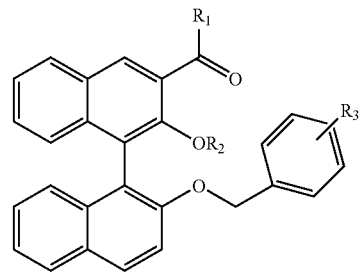

[Chemical Formula I]

wherein R1 and R2 each is Hydrogen, a straight or branched alkyl substitutable with halogen or OH, a cyclic alkyl substitutable with halogen or OH, alkenyl, alkynyl, or an aryl substitutable with halogen or OH; and R3 is NHCXR4 or $NHCHNH_2^+$, wherein X is an oxygen or sulfur atom, and R4 is a straight or branched alkyl substitutable with halogen, NR5R6, or OR7, wherein R5 to R7 each is hydrogen, a straight or branched alkyl substitutable with halogen, or an aryl and if R3 is $NHCHNH_2^+$, the counter ion is halogen ion or $R13COO^-$ wherein R13 is alkyl or aryl.

2. The binaphthol derivative as set forth in claim 1, wherein X is an oxygen atom and R3 is meta-$NHCOCH_3$ or meta-$NHCOC_6H_5$.

3. The binaphthol derivative as set forth in claim 2, wherein R1 and R2 each is a hydrogen atom.

4. The binaphthol derivative as set forth in claim 2, wherein R1 is a hydrogen atom and R2 is CH3.

5. A method for the optical transformation of the L-form amino acids into D-form amino acids, represented by the following chemical formula IV, in which a compound represented by the following chemical formula I of an S-binaphthol derivative is utilized:

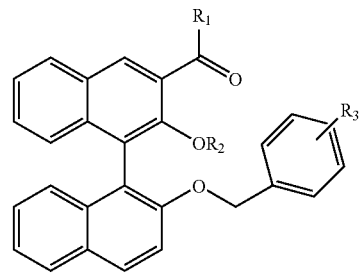

[Chemical Formula I]

wherein R1 and R2 each is Hydrogen, a straight or branched alkyl substitutable with halogen or OH, a cyclic alkyl substitutable with halogen or OH, alkenyl, alkynyl, or an aryl substitutable with halogen or OH; and R3 is NHCXR4 or NHCHNH2, wherein X is an oxygen or sulfur atom, and R4 is a straight or branched alkyl substitutable with halogen, NR5R6, or OR7, wherein R5 to R7 each is hydrogen, a straight or branched alkyl substitutable with halogen, or an aryl and if R3 is $NHCHNH_2^+$, the counter ion is halogen ion or $R13COO^-$ wherein R13 is alkyl or aryl;

$NH_2CHR11COOR12$    [Chemical Formula IV]

wherein R11 is not a hydrogen atom but a monovalent organic group or halogen, and R12 is a hydrogen atom, an alkyl, or an aryl:

wherein said method comprises the steps of:
 providing imine compound by the reaction of amino acids with the compound of chemical formula I;
 transforming L-amino acids into D-amino acids;
 isolating D-amino acids; and
 recycling the compound of chemical formula I.

6. The method as set forth in claim 5, wherein the compound of chemical formula I is an R-binaphthol derivative and is used to transform D-form amino acids into L-form amino acids.

7. The method as set forth in claim 5, wherein X is an oxygen atom, and R3 is meta-$NHCOCH_3$ or meta-$NHCOC_6H_5$.

* * * * *